US009494666B2

(12) United States Patent (10) Patent No.: US 9,494,666 B2
Jeyarajah et al. (45) Date of Patent: Nov. 15, 2016

(54) NMR MEASUREMENT OF CLINICALLY RELEVANT IONIZED BIOSAMPLE CONSTITUENTS SUCH AS IONIZED CALCIUM AND/OR MAGNESIUM

(75) Inventors: Elias Jeyarajah, Raleigh, NC (US); John Contois, Youngsville, NC (US); Lili Duan, Chapel Hill, NC (US); Qun Zhou, Raleigh, NC (US); Steve Markham, Raleigh, NC (US); Dennis Bennett, Shorewood, WI (US); James D. Otvos, Apex, NC (US)

(73) Assignee: LIPSCIENCE, INC., Raleigh, NC (US)

( * ) Notice: Subject to any disclaimer, the term of this patent is extended or adjusted under 35 U.S.C. 154(b) by 1368 days.

(21) Appl. No.: 11/620,868

(22) Filed: Jan. 8, 2007

(65) Prior Publication Data

US 2007/0178598 A1    Aug. 2, 2007

Related U.S. Application Data

(60) Provisional application No. 60/758,272, filed on Jan. 10, 2006, provisional application No. 60/807,942, filed on Jul. 21, 2006.

(51) Int. Cl.
| | |
|---|---|
| G01N 33/48 | (2006.01) |
| G01N 33/50 | (2006.01) |
| G01R 33/465 | (2006.01) |
| G06F 17/10 | (2006.01) |
| G06F 19/12 | (2011.01) |
| G06F 17/14 | (2006.01) |
| G06F 17/15 | (2006.01) |

(52) U.S. Cl.
CPC ............. *G01R 33/465* (2013.01); *G06F 17/10* (2013.01); *G06F 17/14* (2013.01); *G06F 17/15* (2013.01); *G06F 19/12* (2013.01)

(58) Field of Classification Search
None
See application file for complete search history.

(56) References Cited

U.S. PATENT DOCUMENTS 5,460,972 A * 10/1995 Altura et al. .................. 436/79
2002/0177957 A1 * 11/2002 Lee ................................ 702/19

FOREIGN PATENT DOCUMENTS

WO  WO 2005/098463 A2  10/2005

OTHER PUBLICATIONS

Silwood et al. (J. Biol. Inorg. Chem., vol. 7, p. 46-57, 2002).*
Niemela et al. (J. Lab. Clin. Med., vol. 129, No. 1 , p. 89-96, Jan. 1997).*
Jeyarajah (Doctoral thesis, NC State University, pp. 144, 2004).*
Jorde et al. (European Journal of Endocrinology, vol. 141, p. 350-357, 1999).*
Slomp et al. (Crit Care Med, vol. 31, No. 5, p. 1389-1393, 2003).*
Rudnicki et al. (Clinical Chemistry, vol. 38, No. 7, p. 1384, 1992).*
Coen et al. "Proton Nuclear Magnetic Resonance-Based Metabanomics for Rapid Diagnosis of Meningitis and Ventriculitis" CID 41:1582-1590 (2005).
Duan et al. "Automated measurement of ionized Calcium and Magnesium using NMR spectroscopy" Clinical Chemistry 52(6, Suppl. S):A80 (2006) (Abstract).
Hildebrand "7-Least-Squares Polynomial Approximation" *Introduction to Numerical Analysis*, 2$^{nd}$ ed. 314-326 539-567, Martin et al. Ed, McGraw-Hill (1975).
International Search Report for PCT/US2007/00491; Jul. 13, 2007.
Lawson et al. "Solving Least Squares Problems" *SIAM, Philadelphia* 160-165 (1995).
Lindon et al. "Metabonomics: Metabolic Processes Studied by NMR Spectroscopy of Biofluids" *Concepts in Magnetic Resistance* 12(5):289-320 (2000).
Manetti et al. "NMR-based metabonomic study of transgenic maize" *Phytochemistry* 65:3187-3198 (2004).
Nicholson et al. "High resolution $^{1}$ H n.m.r. studies of vertebrate blood and plasma" *Biochem J.* 211:605-615 (1983).
Rayana et al. "Guidelines for sampling, measuring and reporting ionized magnesium in undiluted serum, plasma or blood" Clin Chem Lab Med 43(5):564-569 (2005).
Shirey, T., Importance and Interpretation of Ionized Magnesium (iMg) Activity in Acutely and Chronically Ill Patients, Abstract No. 102 (Abstract only), Nova Biomedical, Feb. 2000.
Somashekar et al. "Simple pulse-acquire NMR methods for the quantitative analysis of calcium, magnesium and sodium in human serum" *Spectrochimica Acta Part A* 65:254-260 (2006).
Toffaletti "Calcium, Magnesium and Phosphate" Chapter 20, 392-406 *Clinical Laboratory Medicine* Kenneth D. McClatchey, M.D., D.D.S., Ed. Lippincott Williams & Wilkins (2001).
International Preliminary Report on Patentability mailed Jul. 15, 2008 for International Patent Application PCT/US2007/000491.

* cited by examiner

*Primary Examiner* — Russell S Negin
(74) *Attorney, Agent, or Firm* — Kilpatrick Townsend & Stockton LLP

(57) ABSTRACT

Methods, computer program products, NMR assays and automated/semi-automated systems measure concentrations of ionized calcium and/or magnesium or other metabolites in clinical biosamples using NMR data obtained from an NMR spectrometer, such as a clinical NMR Analyzer.

14 Claims, 10 Drawing Sheets

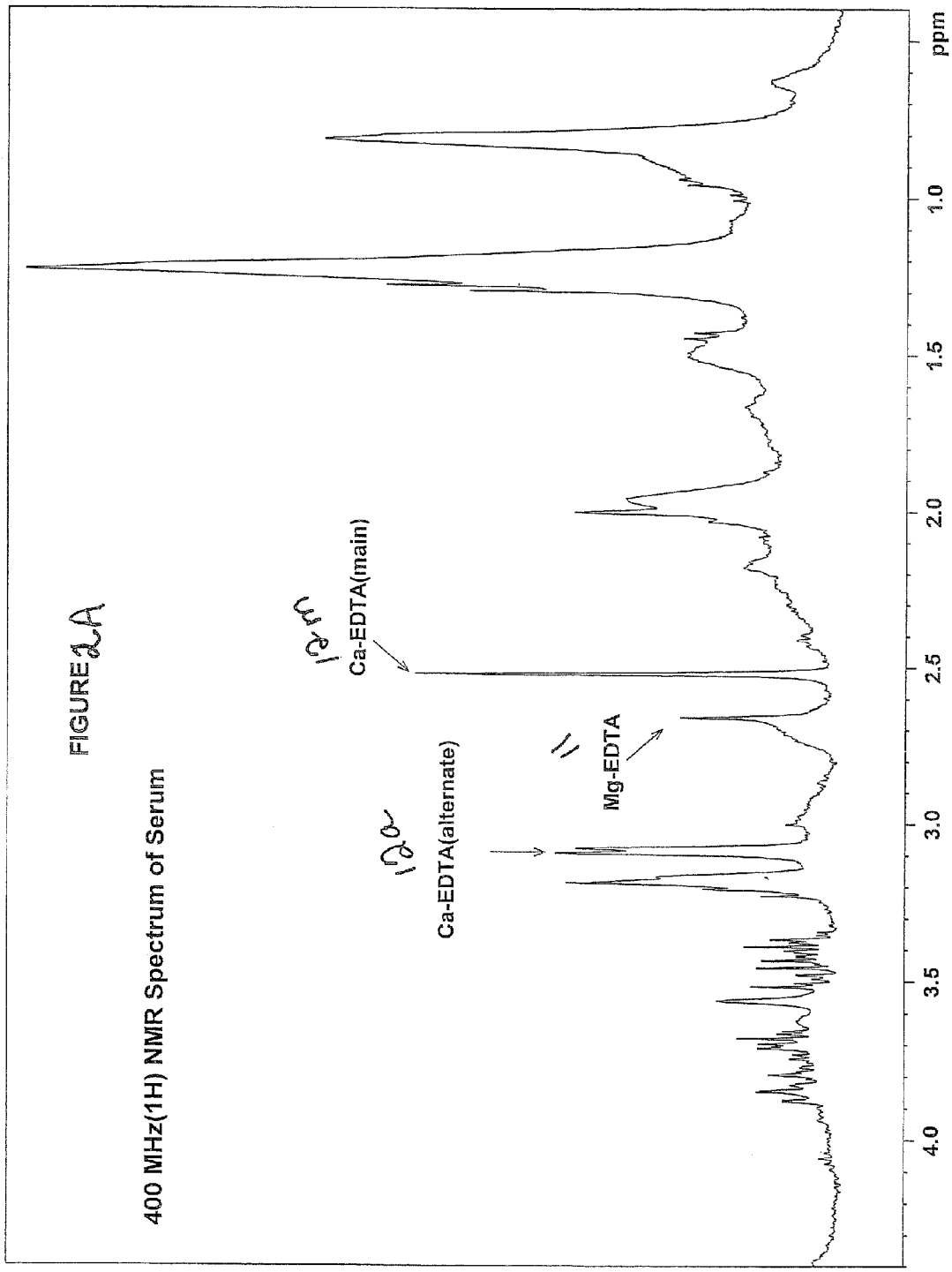

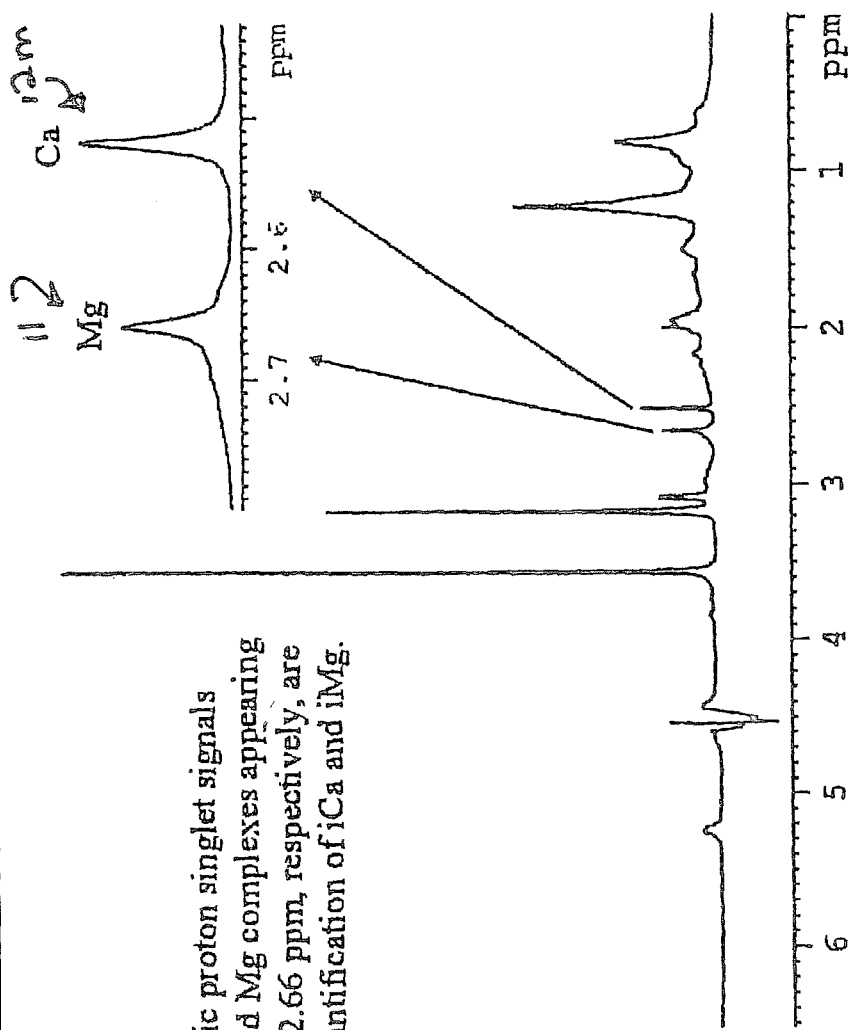
Figure 2 NMR spectrum of a serum sample
The ethylenic proton singlet signals of the Ca and Mg complexes appearing at 2.52 and 2.66 ppm, respectively, are used for quantification of iCa and iMg.

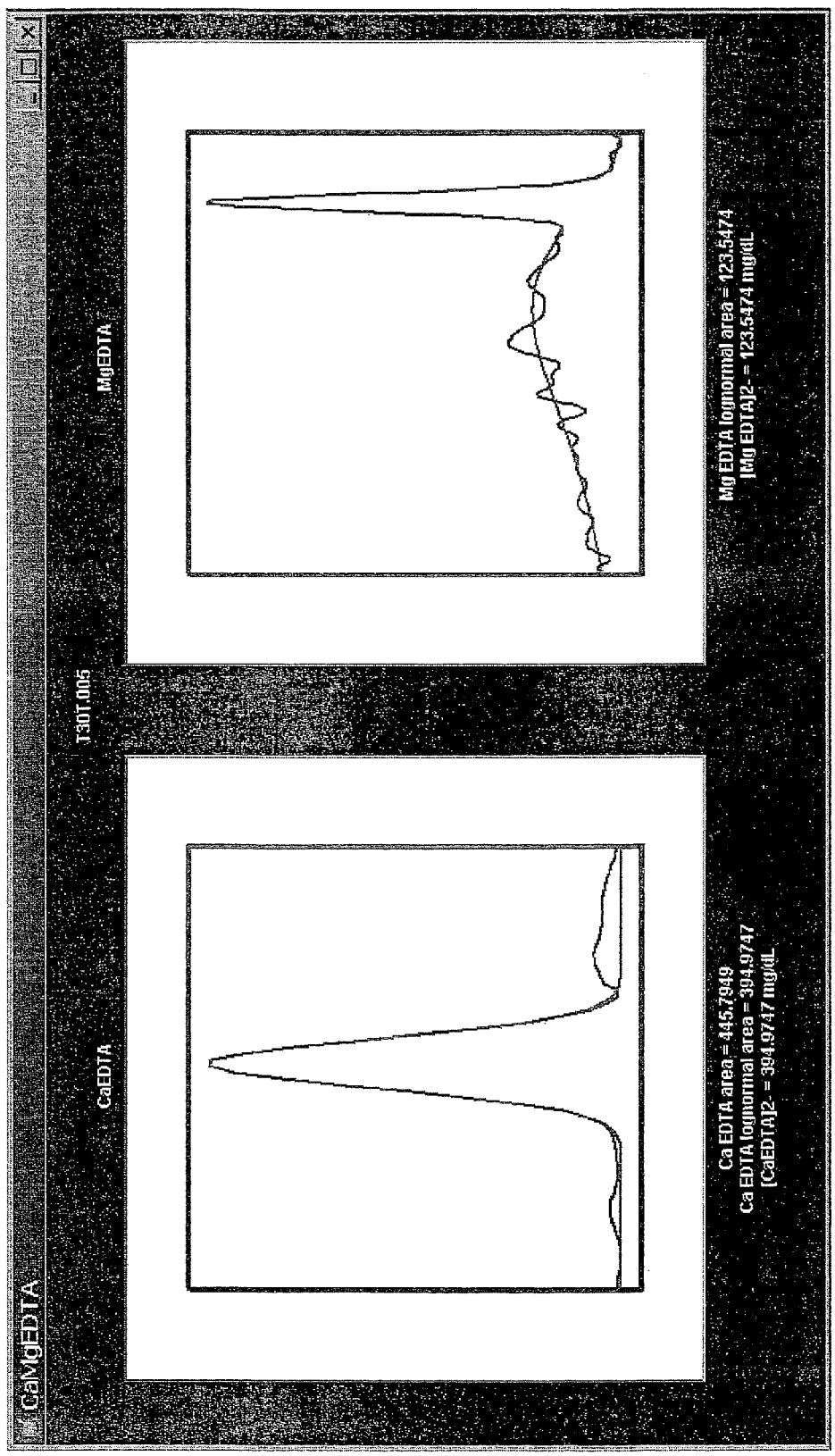

NMR MEASUREMENT OF CLINICALLY RELEVANT IONIZED BIOSAMPLE CONSTITUENTS SUCH AS IONIZED CALCIUM AND/OR MAGNESIUM

RELATED APPLICATIONS

This application claims priority to U.S. Provisional Application Ser. No. 60/758,272, filed Jan. 10, 2006 and U.S. Provisional Application Ser. No. 60/807,942, filed Jul. 21, 2006, the entire contents of the above-referenced documents are hereby incorporated herein by reference as if recited in full herein.

FIELD OF THE INVENTION

The present invention relates generally to NMR analysis of biosamples.

BACKGROUND OF THE INVENTION

Total calcium (Ca) and Magnesium (Mg) levels are relatively easily measured using AA, MS or spectrophotometry. Unfortunately, the quantification of clinically relevant ionized Ca and Mg (i-Ca, i-Mg) is more difficult. Currently, i-Ca and i-Mg are measured using potentiometry with ion-selective electrodes (ISE), which is sensitive to physical and biological conditions.

There is a need for alternate measurement options for evaluating clinically relevant ionized constituents in biosamples.

SUMMARY OF EMBODIMENTS OF THE INVENTION

Embodiments of the present invention are directed to automated or semi-automated NMR measurement of clinically relevant ionized constituents of biosamples.

The NMR evaluation can be used to determine the concentrations of i-Ca or i-Mg in a biosample.

Embodiments of the present invention are directed to evaluating a biosample that has a suitable reagent(s) added thereto, the reagent selected for its ability to react with metabolite(s) in biological samples to produce an NMR signal that can be used for quantitation of the metabolite(s).

Some embodiments are directed to methods of measuring ionized constituents in a biosample. The methods include: (a) obtaining NMR signal data from a proton NMR spectrum of a biosample; and (b) programmatically determining the concentration of at least one of ionized calcium or ionized magnesium in the biosample based on the obtained NMR data.

In some embodiments, the concentrations of both i-Ca and i-Mg can be determined using NMR signal data from the same aliquot of sample and/or with the same NMR proton spectrum, without affecting the reliability of the measurements of either i-Ca or i-Mg.

Other embodiments are directed to automated methods of evaluating a biosample for levels of ionized calcium and ionized magnesium. The methods include programmatically calculating the concentration of ionized calcium and ionized magnesium in an in vitro biosample using NMR data from an NMR proton spectrum of the biosample.

Still other embodiments are directed to clinical NMR systems configured to automatically determine the concentrations of ionized calcium and ionized magnesium in patient biosamples. The systems include: (a) a sample handler for serially presenting respective biosamples to an input port; (b) an enclosed flow path configured to serially flow the respective biosamples presented by the automated sample handler, wherein the enclosed flow path includes a non-magnetic flow cell; (c) an NMR detector in communication with an NMR flow probe, the NMR detector comprising a high-field cryogenically cooled superconducting magnet with a magnet bore having an opposing top and bottom, the flow probe configured to generally reside in the magnet bore, wherein the flow cell is configured and sized to extend into the magnet bore and direct the samples to serially flow from one of the top or bottom of the magnet bore into the magnet bore proximate the flow probe during operation; and (d) a signal processor configured to obtain and analyze NMR signal spectra of the biosamples to determine quantitative measurements of ionized calcium and ionized magnesium in the respective biosamples.

Other embodiments are directed to NMR assays for clinical evaluation. The assays include a blood plasma or serum biosample and a chelating agent mixed with the blood plasma or serum sample (or urine, CSF or other biosample). The chelating agent is also configured to generate first and second NMR proton signal peaks of the chelated biosample in different predetermined regions of an NMR spectrum. The signal peak in the first region corresponding to concentration of ionized calcium and the signal peak in the second region corresponding to concentration of ionized magnesium in the biosample.

Still other embodiments are directed to computer program products for determining concentrations of ionized constituents in respective patient plasma and/or serum samples. The computer program product includes a computer readable storage medium having computer readable program code embodied in the medium. The computer-readable program code includes: (a) computer readable program code configured to obtain a proton NMR composite spectrum of a biosample, the proton NMR composite spectrum comprising an ethylenic proton singlet peak region for ionized calcium and ionized magnesium; and (b) computer readable program code configured to determine the concentration of ionized calcium and ionized magnesium in the biosamples using data from the NMR spectrum.

Still other embodiments are directed to NMR quantiation systems. The systems include: a chelating agent mixed with a target biosample, wherein the chelating agent is also configured to generate electronically detectable first and second NMR proton signal regions in a proton NMR spectrum of the chelated biosample, each region having at least one predetermined signal peak region associated with a respective complex of ionized calcium and ionized magnesium; and a processor configured to analyze the NMR proton spectrum to calculate: (a) a concentration of ionized calcium in the biosample using data associated with the at least one signal peak in the first region of the NMR; and (b) a concentration of ionized magnesium in the biosample using data associated with the at least one signal peak in the second region.

As will be appreciated by those of skill in the art in light of the present disclosure, embodiments of the present invention may include methods, assays, systems, apparatus and/or computer program products or combinations thereof.

The foregoing and other objects and aspects of the present invention are explained in detail in the specification set forth below.

BRIEF DESCRIPTION OF THE FIGURES

FIG. 2A is an NMR proton spectrum of serum illustrating NMR regions of interest that can be used to determine concentration of i-Ca and i-Mg according to embodiments of the present invention.

FIG. 2B is an NMR spectrum of a serum sample illustrating ethylenic proton singlet signals of Ca and Mg complexes appearing at 2.52 and 2.66 ppm, respectively, according to embodiments of the present invention.

FIGS. 3A and 3B are graphs of Ca-EDTA and Mg-EDTA deconvolution signals, respectively, of a proton NMR spectrum of a serum sample according to embodiments of the present invention.

FIG. 7B is a graph of the distribution of Ionized Magnesium in Men and Women (frequency versus iCa mM), with the broken line representing women.

DETAILED DESCRIPTION OF EMBODIMENTS OF THE INVENTION

Figure 1:
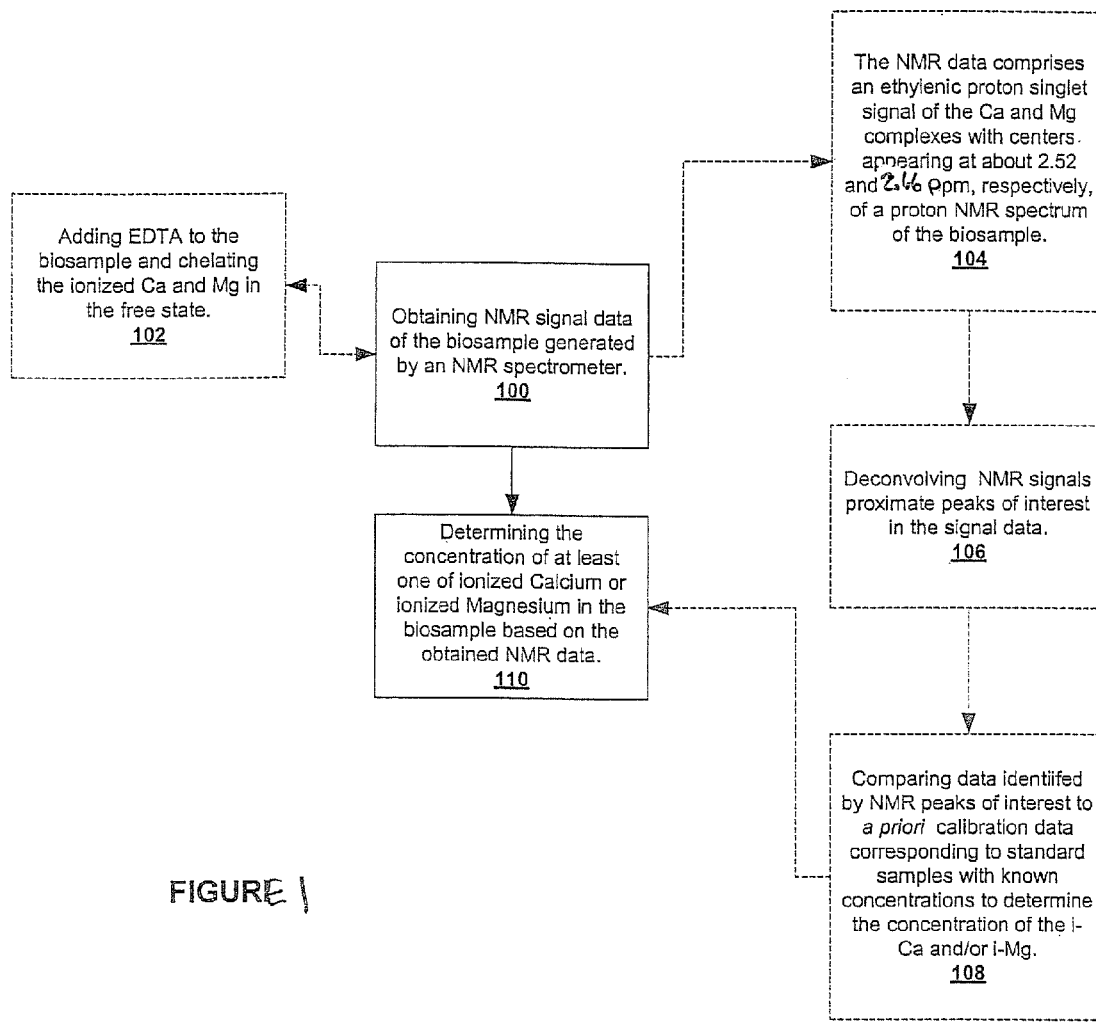
FIG. 1 is a flow chart showing operations that can be used to measure ionized clinically relevant constituents in a biosample according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The term "programmatically" means carried out using computer program directed operations. The terms "automated" and "automatic" means that the operations can be carried out with minimal or no manual labor or input. The term "semi-automated" refers to allowing operators some input or activation, but the calculations and signal acquisition as well as the calculation of the concentrations of the ionized constituent(s) is done electronically, typically programmatically, without requiring manual input.

The terms "complexes" or "complex" (such as "calcium and/or magnesium complexes") refer to the bound form of the target, ionized constituent. For example, where EDTA is the chelating agent that binds/chelates divalent metal ions, the bound form of Ca-EDTA or Mg-EDTA is referred to as a "complex". The complex generates a detectable NMR peak region that can be used to determine the concentration of the constituent/metabolite in the chelated biosample. It is noted that any chelators of divalent metal ions can be used, for example, EDTA, EGTA (Ethylene Glycol-bis(beta-aminoethyl-ether)-N,N,N',N'-TetraAcetate), GEDTA (Glycoletherdiamine-N,N,N',N'-tetraacetic Acid), and the like.

Different amounts of chelators can be added to the biosample to obtain suitable NMR signals. For some chelators, concentrations can range between about 2 mM to about 20 mM. The concentration should be selected to complex the entire $Mg^{2+}/Ca^{2+}$ ions without over concentrating the sample, which may have some adverse effects. In some embodiments, a 10 mM amount can be used so that substantially all physiologically encounterable levels of Ca/Mg are complexed.

For embodiments employing automated NMR clinical analyzers to obtain quantitative analysis measurements that can be used for in vitro diagnostics, the automated NMR analyzers can be configured to meet governmental medical regulatory requirements such as those described in applicable federal regulations, including those in 21 CFR (such as 21 CFR 820 and 21 CFR 11) for medical devices. The NMR analyzers can include interactive sample handlers that communicate with the NMR spectrometer and/or remote control system. The NMR clinical analyzers can be configured to reliably run and obtain quantified clinical measurements for diagnostic tests on high volume throughput of biosamples while reducing the amount of operator input or labor required to operate the automated analyzers. The NMR analyzers can be constructed and/or configured in such a manner as to be able to obtain PMA (pre-market approval) and/or 510(k) approval from the United States Food and Drug Agency ("USFDA") and/or corresponding foreign agencies. A suitable NMR analyzer expected to be commercially available in the near future is the NUMERA™ clinical analyzer from LipoScience, Inc., located in Raleigh, N.C.

Proton nuclear magnetic resonance ($^1$H-NMR) may be used for identification and quantification of any number of proton-containing metabolites or drugs, including amino and organic acids associated with inborn errors of metabolism, therapeutic drugs and drugs of abuse, and markers for lipid and lipoprotein disorders. See, e.g., (a) Manetti C, Bianchetti C, Bizzarri M, et al: *NMR-based metabonomic study of transgenic maize, Phytochemistry.* 2004 December; 65(24): 3187-98; and (b) Coen M, O'Sullivan M, Bubb W A, et al: *Proton nuclear magnetic resonance-based metabonomics for rapid diagnosis of meningitis and ventriculitis*, Clin Infect Dis. 2005 Dec. 1; 41(11):1582-90.

Particular embodiments of the instant invention may provide automated assays for measuring ionized calcium (iCa) and ionized magnesium (iMg) using $^1$H-NMR. It is well known that iCa and iMg are the biologically active and clinically relevant forms. Both iCa and iMg have important physiological functions and are important for diagnosis and monitoring in a variety of patient care settings, including the assessment and monitoring of critical care patients. See, e.g., (a) Toffaletti J G: *Calcium, magiesium, and phosphate, in: Clinical Laboratory Medicine,* 2nd Ed., McClatchey K D, Ed. Williams and Wilkins, Baltimore, Md. 2001; and (b) Shirey T.: *Importance and interpretation of ionized magnesium (iMg) activity in acutely and chronically ill patients*, Nova Biomedical, July 2001.

One current method of measuring iCa and iMg is potentiometry using ion-selective electrodes (ISE). This assay, however, may suffer from extreme sensitivity to physical and biological conditions. See, e.g., Rayana M C et al., *Guidelines for sampling, measuring and reporting ionized magnesium in undiluted serum, plasma or blood*, Clin Chem Lab Med 2005 43 (5) 564-9. It is believed that the conventional iMg assays are insufficiently selective, and several ions, including calcium, may interfere with measurement or identification.

The NMR assays of the instant invention can provide a sensitive, precise and automated technical solution for measuring clinically relevant bioconstituents, such as, for example, ionized calcium and ionized magnesium directly in serum and plasma samples. Unlike the ISE method, iMg measurement is substantially, if not totally, unaffected by the presence of iCa.

As will be appreciated by one of skill in the art, the present invention may be embodied as an apparatus, an assay, an assay kit, a method, a data or signal processing system, and/or a computer program product. Accordingly, the present invention may take the form of an entirely software embodiment, an assay for chemical analysis, or embodiments combining, chemical, software and hardware aspects. Furthermore, certain embodiments of the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, but is not limited to, an electronic, magnetic, optical, superconducting magnetic, infrared, or semiconductor system, apparatus, device, or propagation medium. More specific examples (a nonexhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium, upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as Java®, Smalltalk, Python, Labview, C++, or VisualBasic. However, the computer program code for carrying out operations of the present invention may also be written in conventional procedural programming languages, such as the "C" programming language or even assembly language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The flowcharts and block diagrams of certain of the figures herein illustrate the architecture, functionality, and operation of possible implementations of analysis models and evaluation systems and/or programs according to the present invention. In this regard, each block in the flow charts or block diagrams represents a module, segment, operation, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

Embodiments of the present invention may be used to analyze any in vitro biosample. The biosample may be in a fluid, liquid, solid, and/or semi-solid form. The biosample may include tissue, blood, biofluids, biosolids and the like. In some embodiments, the biosample is a serum or plasma sample obtained from human blood. Fasting is not required. The biosample can be stored, held and/or run at room temperature or refrigerated. The lifetime of the room temperature sample for this assay is not yet determined. Although described herein primarily with respect to a human blood or serum sample, the same NMR methodology can be adopted to urine and other biological fluids for the measurement of ionized Ca/Mg or other clinically relevant constituents. Embodiments of the present invention are directed to adding any reagents to biological samples that will react with metabolites of clinical relevance in biological samples to produce an NMR signal that can be used for quantitation of the metabolite. In the examples herein, both Ca and Mg are divalent. In blood, there is bound Ca/Mg and free or ionized Ca/Mg. The bound part is in the proteins (mostly albumin). Measurements of unbound or ionized parts can be clinically meaningful for several disease states.

Referring now to FIG. 1, operations that can be used to evaluate a biosample in a relatively automated manner is illustrated. As shown, NMR signal data of a biosample is obtained using an NMR spectrometer (block 100). The concentration of at least one of ionized Calcium or Magnesium in the biosample is determined based on the obtained NMR data (block 110). The NMR assay provides a sensitive, precise and automated (or semi-automated) technical solution for measuring ionized Ca and ionized Mg directly in serum samples. Unlike the ISE method, ionized Mg measurement is unaffected by the presence of ionized Ca and each can be measured using data from the same sample, typically using different regions of interest from the same NMR proton spectrum.

In some embodiments, controlled chelating conditions can include maintaining a suitable pH (such as a pH of about 7.4) and a suitable temperature (room temp 20-25 deg C. for chelating, then about 47 deg C. for NMR measurement). Sample handling conditions may be similar to lipoprotein sample handling conditions. It is noted that it is believed that the Ion Selective Electrode (ISE) method is difficult to standardize and generally needs to be calibrated for low and high values every time and can be very sensitive to ionic strength, pH, temperature, liquid junction potentials etc. Sample volume for a standard assay is typically about 150 µL. However, it is contemplated that sample sizes of as little as about 25 µL can be used doing appropriate dilutions to fill the NMR measurement cell. Thus sample sizes may be between about 25 µL to about 150 µL.

Any suitable chelator and/or chelators of divalent metal ions, such as Ethylenediaminetetraaceticacid (EDTA), can be added to the biosample to chelate the ionized Ca and Mg in the free state (block 102). The NMR data can an NMR proton spectrum with ethylenic proton singlet signals of the Ca and Mg appearing at about 2.52 ppm and about 2.66 ppm, respectively, of the proton NMR spectrum (using a 400 MHz NMR clinical analyzer) (block 104). Of course different frequency NMR systems may be used as is well known to those of skill in the art.

FIGS. 2A and 2B illustrate an exemplary NMR spectrum with the two primary regions of interest, the first NMR proton singlet region of interest 11, at about 2.66 ppm for measuring i-Mg and the second primary NMR proton singlet region of interest 12m at about 2.52 ppm for measuring i-Ca. FIG. 2A also shows an alternative doublet region at 12a that can be used with or as an alternative to the primary 12m region for calcium. That is, in some embodiments, such as where the primary peak region 12m may be superimposed by an interference peak, the alternate Ca-EDTA peak region 12a appears as a doublet at about 3.08 ppm. This is an acetate peak of Ca-EDTA (as opposed to the ethylenic peak at 2.52 ppm). Other peaks may be appropriate if other additives (chelators) are used for the analysis.

It will be appreciated that the region(s) of interest in the spectrum can shift with different field strength NMR spectrometers. Examples of suitable NMR analyzers are described in co-pending, co-assigned, U.S. patent application Ser. No. 11/093,596, entitled, NMR Clinical Analyzers and Related Methods, Systems, Modules and Computer Programs for Clinical Evaluation of Biosamples, the contents of which are hereby incorporated by reference as if recited in full herein.

Referring back to FIG. 1, NMR data, associated with peaks of interest in the signal can be deconvolved (block 106). Exemplary deconvolution methods are described in co-pending, co-assigned, U.S. patent application Ser. No. 10/691,103, Filed Oct. 22, 2003, entitled, Methods, Systems and Computer Programs for Deconvolving the Spectral Contribution of Chemical Constituents with Overlapping Signals, the contents of which are hereby incorporated by reference as if recited in fall herein. See also, Lawson, C. L., Hanson, R. J. *Solving Least Squares problems*. Philadelphia, Pa.: SIAM, 1995, pp. 160-165, describing techniques related to deconvoluting lineshapes using multivariate analysis with non-negative constraints.

Data (such as area data) associated with one or more NMR peaks of interest can be compared to a priori calibration data corresponding to standard samples with known concentrations to automatically, electronically (programmatically) determine the concentration of the i-Ca and/or i-Mg in patient samples. The fully (or semi) automatable i-Ca/i-Mg assays can be run on any suitable sample size, including relatively small samples, such as between about 25 microliters (µL) to about 500 µL, typically about ~150 µL samples. The NMR interrogation or signal acquisition of the sample can be relatively quick, such as in less than one minute, typically between about 10-45 seconds, and more typically about ~40 s of NMR time. The normal ranges in blood serum/plasma are typically between about 8.2-10.0 mg/dL for i-Ca, and typically between about 1.9-2.7 mg/dL for i-Mg. Embodiments of the present invention can determine concentrations in the "normal" ranges noted as well as above and below same. For example, up to about 24 mg/dL for i-Ca and up to about 9.7 mg/dL for i-Mg.

In some embodiments, an automated or semi-automated clinical NMR analyzer can serially analyze one in vitro blood serum and/or plasma biosample, or subsets of related biosamples, to determine the concentration of ionized constituents (such as i-Ca and/or i-Mg) as well as lipoproteins. That is, the potential exists for doing the lipoprotein assay and i-Ca/i-Mg on the same sample. However, this will involve changes to the lipoprofile assay in terms of what buffers will be used for diluting the sample. In other embodiments, a separate aliquot of the biosample can be used to which the appropriate reagent will be added and the i-Ca/i-Mg assay performed. The i-Ca and i-Mg can however be measured from the same spectrum and can be carried out so that the two measurements are generated substantially simultaneously.

As is known regarding lipoprotein measurement, the lineshape of the whole plasma spectrum is dependent on the relative amounts of the lipoprotein subclasses whose amplitudes change (sometimes dramatically) with their relative concentrations in the plasma sample. Since the observed $CH_3$ lineshapes of whole plasma samples are closely simulated by the appropriately weighted sum of lipid signals of their constituent lipoprotein classes, it is possible to extract the concentrations of these constituents present in any sample. This is accomplished by calculating the weighting factors, which give the best fit between observed blood plasma NMR spectra and the calculated blood plasma spectra.

Generally speaking, the NMR lipoprotein analysis can be carried out by the following steps: (1) acquisition of an NMR "reference" spectrum for each of the "pure" individual of constituent lipoprotein classes and/or subclasses of plasma or serum of interest and/or related groupings thereof; (2) acquisition of a whole plasma or serum NMR spectrum for a sample using measurement conditions substantially identical to those used to obtain the reference spectra; and (3) computer deconvolution of the NMR spectrum in terms of the constituent classes and/or subclasses (or related groupings thereof) to give the concentration of each lipoprotein constituent expressed as a multiple of the concentration of the corresponding lipoprotein reference.

Although the procedure can be carried out on lipoprotein classes, carrying out the process for subclasses of lipoproteins can decrease the error between the calculated lineshape and the NMR lineshape, thus increasing the accuracy of the measurement while allowing for simultaneous determination of the subclass profile of each class. Because the differences in subclass lineshapes and chemical shifts are small, it is typically important to correctly align the reference spectrum of each subclass with the plasma spectrum.

The alignment of these spectra can be accomplished by the alignment of control peaks in the spectra, which are known to respond in the same manner to environmental variables, such as temperature and sample composition, as do the lipoprotein spectra. As is known, one such suitable alignment peak is the peak produced by CaEDTA found in prepared (diluted) sample mixtures, although other EDTA peaks or suitable peak may be utilized. By alignment of the spectra, the small variations in the subclasses' lineshapes and chemical shifts may be used to produce higher accuracy and subclass profiles. Further description of these methods can be found in U.S. Pat. Nos. 4,933,844 and 5,343,389 to Otvos, the contents of which are hereby incorporated by reference as if recited in full herein. The mathematics used in the lineshape fitting process (i.e., least squares fit of an unknown function in terms of a weighted sum of known functions) is well known and is described in many textbooks of numerical analysis, such as F. B. Hildebrand, *Introduction to Numerical Analysis,* 2nd edition, pp. 314-326, 539-567, McGraw-Hill, 1975.

Figure 4A:
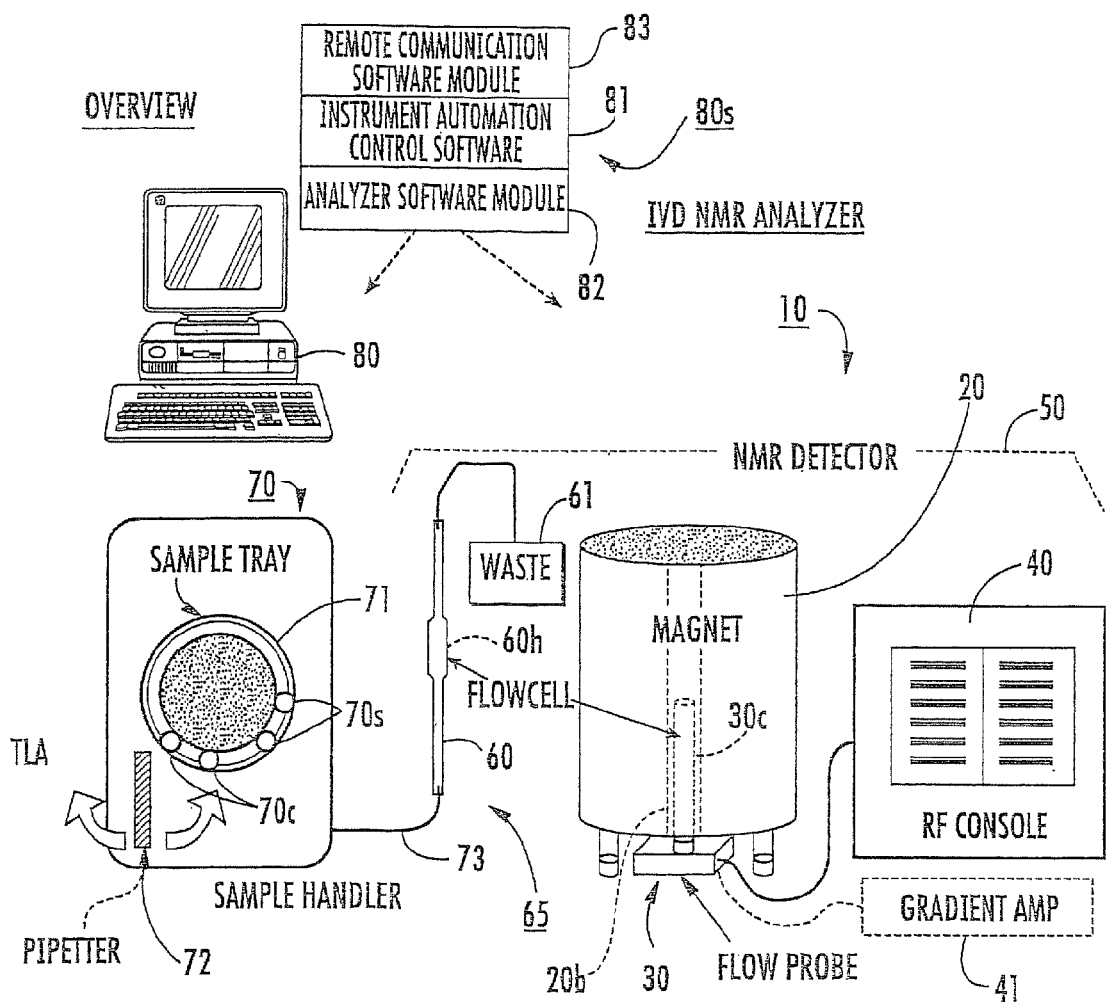
FIG. 4A is a schematic illustration of an in vitro diagnostic NMR analyzer according to embodiments of the present invention.
Figure 4B:
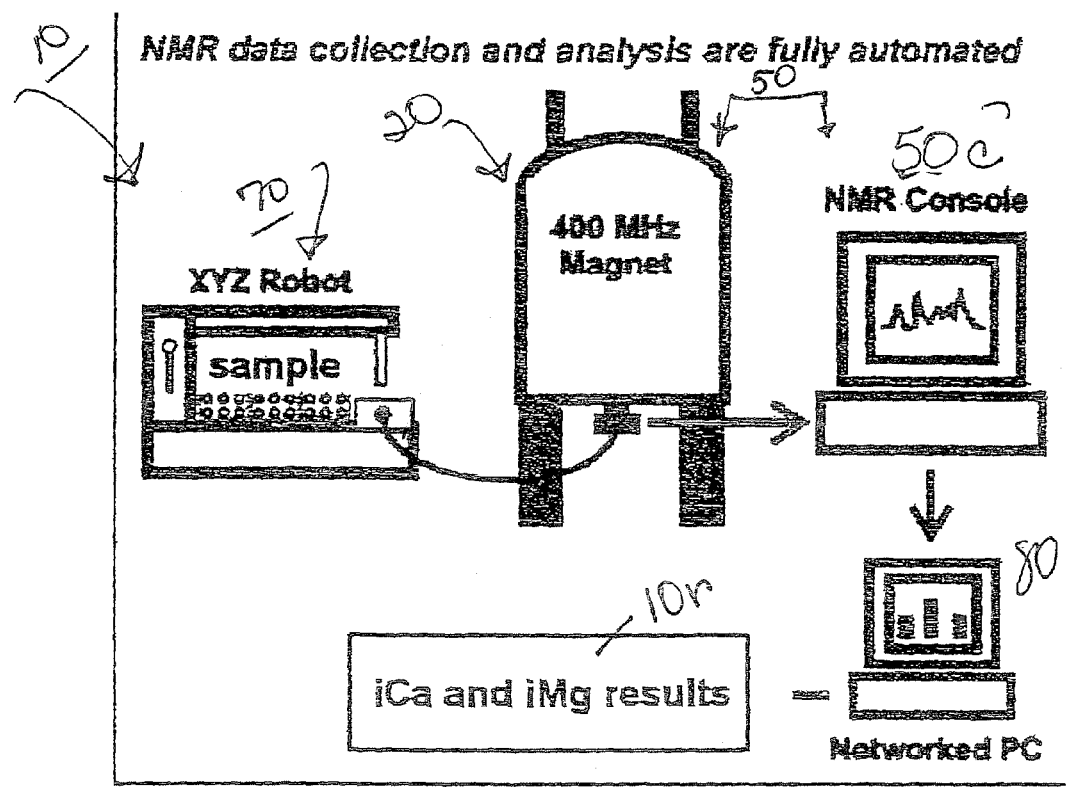
FIG. 4B is a block diagram illustration of a clinical NMR analyzer according to embodiments of the present invention.
Figure 6A:
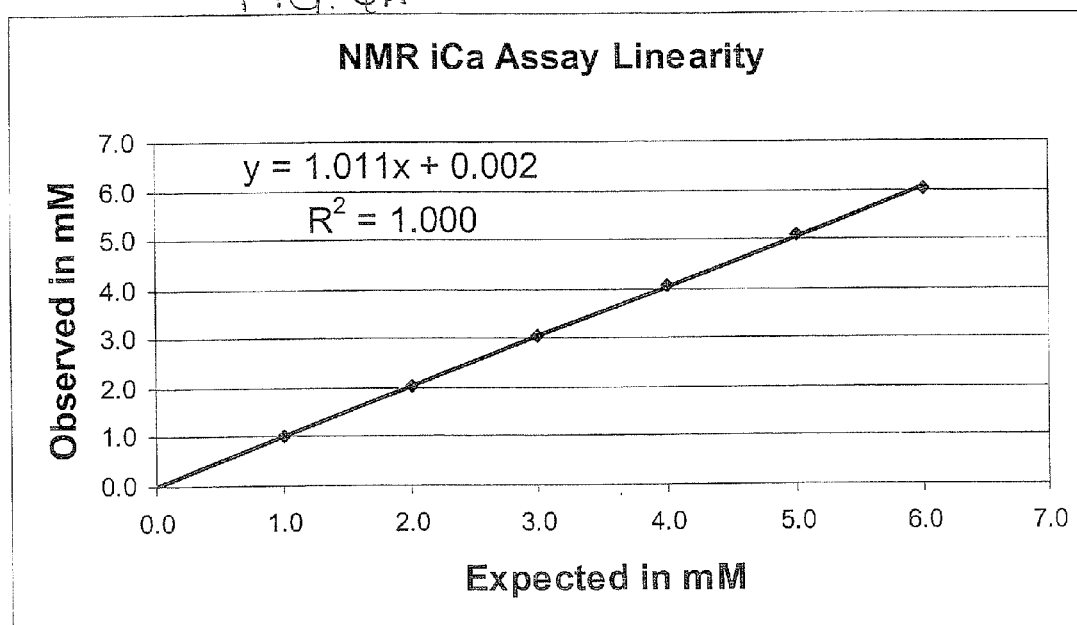
FIG. 6A is a graph of NMR iCA Assay Linearity expressed in observed in mM versus Expected in mM.
Figure 6B:
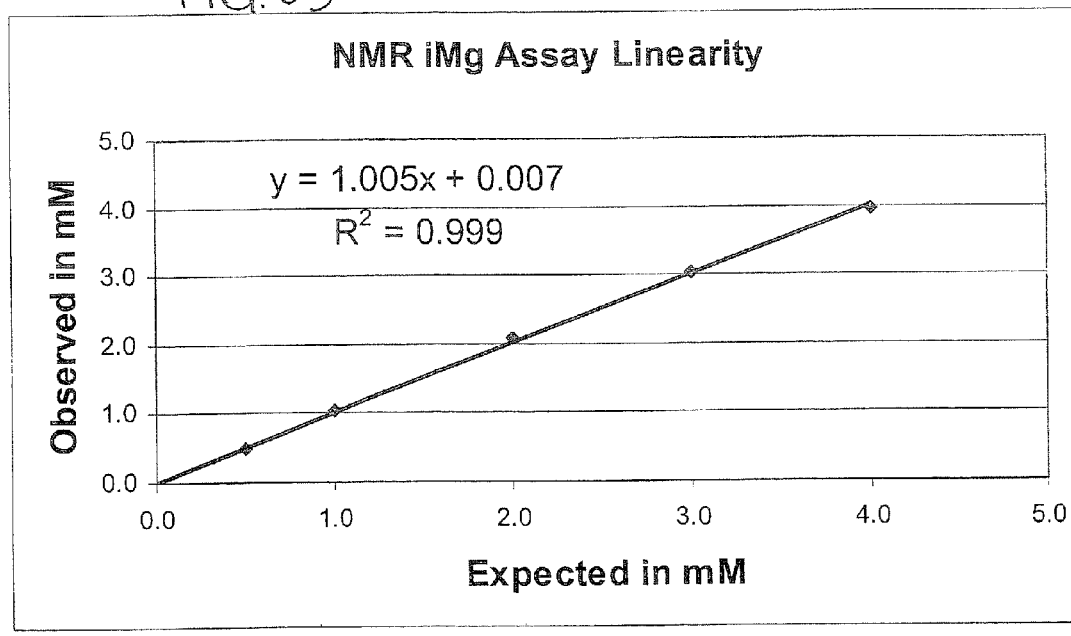
FIG. 6B is a graph of NMR iMg Assay Linearity expressed in observed in mM versus Expected in mM

FIG. 4A illustrates a schematic diagram of one example of an in vitro diagnostic clinical NMR analyzer 10. However, the scope of the invention is not limited to this spectrometer configuration. As shown, the analyzer 10 includes an NMR detector 50, an enclosed flow path 65, an automated sample handler 70, and a controller/processor 80 (shown as a CPU) with operational software 80s. The term "NMR detector" may also be known as an NMR spectrometer as will be appreciated by those of skill in the art. The NMR detector 50 includes a magnet, typically a cryogenically cooled high field superconducting magnet 20, with a magnet bore 20b, a flow probe 30, and RF pulse generator 40. FIG. 4B illustrates that the NMR detector 50 can also include an NMR console 50c that communicates with the controller 80 over a computer network and that the system 10 can generate a test report 10r of iCa and iMg measurement results of in vitro samples. The testing system can be configured to define gender-specific "acceptable" or "normal" measurements, such as gender-specific (different) ranges and/or mean values, particularly for iCa measurements. For example, as shown in FIG. 6A, men may be expected to have higher mean iCa measurements relative to women which may indicate calcium deficiencies in women or just lower normal values. FIG. 6B illustrates that while the measured range may be similar between men and women the mean for men is lower than that for women.

The term "high-field" magnet refers to magnets that are greater than 1 Tesla, typically greater than 5 Tesla, and more typically greater than about 9 Tesla. Magnetic fields greater than about 13 Tesla may, in some situations, generate broader lineshapes, which in some analysis of some biosamples, may not be desirable. As stated above, one particularly suitable NMR detector 50 is the 9.4 Tesla AVANCE INCA™ system (an integrated NMR chemical analyzer) from Bruker BioSpin Corp., located in Billerica, Mass. The flow probe 30 is in communication with the RF pulse generator 40 and includes an RF excite/receive circuit 30c, such as a Helmholtz coil. However, as will be appreciated by those of skill in the art, other excite/receive circuit configurations may also be used.

It is noted that although illustrated as a system that serially flows biosamples using a flow cell 60, other sample handlers 70 and biosample introduction means can be used. For example, the biosample can be processed as it is held in a respective tube or other sample container (not shown). In some embodiments, each of the modular components of the NMR analyzer 10 may be sized and configured to fit within a single housing or enclosure.

Field homogeneity of the detector 50 can be adjusted by shimming on a sample of about 99.8% $D_2O$ until the spectral linewidth of the HDO NMR signal is less than 0.6 Hz. The 90° RF excitation pulse width used for the $D_2O$ measurement is typically about 6-7 microseconds. Other shimming techniques can also be used. For example, the magnetic field can be automatically adjusted based on the signal lineshape and/or a width or height thereof. The NMR detector 50 may optionally include a gradient amplifier in communication with gradient coils 41 held in the magnet bore 20b as is well known to those of skill in the art, and the gradient system may also be used to help shim the magnet.

During operation, the flow probe 30 is held inside the magnet bore 20b. The flow probe 30 is configured to locate the flow probe RF circuitry 30c within the bore 20b to within about +/−0.5 cm of a suitably homogeneous portion of the magnetic field $B_0$. The flow probe 30 is also configured to receive the flow cell 60 that forms part of the biosample enclosed flow path 65. The flow cell 60 typically includes a larger holding portion 60h that aligns with the RF circuitry 30c of the flow probe 30. The flow cell 60 is configured to remain in position with the holding portion 60h in the magnet bore 20b and serially flow biosamples to the holding portion 60h, with successive biosamples being separated by a fluid to inhibit cross-contamination. The biosample is typically held in the holding portion 60h for between about 30 seconds to about 5 minutes during which time a proton NMR spectrum is obtained and electronically correlated to the sample accession number or identifier (i.e., a patient identifier). Data from a single NMR spectrum (or multiple NMR spectrums if desired) can be used to calculate the i-Ca and/or iMg concentrations as well as the lipoprotein values as noted above. The flow cell 60 can be formed of a non-magnetic material that does not degrade the performance of the NMR detector 50. Typically, the flow cell 60 is formed of an aluminosilicate material such as glass; however, other magnetic-friendly non-porous materials may be used including ceramics, elastomers, and the like.

A magnetically-friendly optic viewing scope (such as a fiber optic system) may be used to allow a user and/or the system 10 to visually monitor conditions in the magnet bore 20*b* (i.e., position of the probe, leaks or the like) (not shown). The viewing scope can be mounted to the bore or made integral to the flow cell 60 or the flow probe 30. Similarly, at least one leak sensor can be placed to automatically detect fluid leakage, whether biosamples, cleansers or cryogens. If the former, a leak sensor can be used to detect leaks caused by flow path disruption; if the latter a gas sniffer type sensor can be used. Cryogen level sensors can also be used to monitor the level of the liquid (helium and/or nitrogen) to allow for automated supply orders, identification of an increased use rate (which may indicate a wire or problem), and the like.

In the embodiment shown, the flow cell 60 is in fluid communication with a waste receptacle 61 at one end portion and a sample intake 73 on the other end portion. In certain embodiments, the analyzer 10 is configured to flow the samples from top to bottom using a flow cell 60 that has a major portion that is substantially straight (i.e., without bends) to reduce the length of the flow path 60 and/or to reduce the likelihood that the bends in a flow path will block the flow. In some embodiments, the flow cell 60 is entirely straight. In particular embodiments, the entire flow path 65 may be straight throughout its length (including portions upstream and downstream of the flow cell 60, from intake to discharge into the waste container). In other embodiments, elastomeric conduit and/or tubing (which may comprise TEFLON) can be used to connect the flow cell 60 to the sample intake portion of the flow path 65 and the conduit and/or tubing may be bent to connect to mating components as desired. However, it the conduit/tubing extend into the magnet bore 20*b*, then that part of the flow path 65 may also be configured to be straight as discussed with respect to the flow cell 60.

In some embodiments, the flow cell 60 has an inner diameter of between about 0.5 mm to about 0.8 mm upstream and downstream of the holding portion 60*h*. The downstream portion is typically at least about 0.8 mm to inhibit clogs in the flow system. The holding portion 60*h* may have a diameter that is between about 0.2 mm to about 0.6 mm.

The biosamples may be configured in appropriate sample volumes, typically, for blood plasma or serum, about 0.5 ml. For whole plasma, a reduced sample size of about 50-300 microliters, typically about 60-200 microliters, and more typically between about 60-150 microliters may be desired. The sample flow rate may be between about 2-6 ml/min to flow the sample to the holding portion 60*h* for the NMR data collection and associated analysis.

Still referring to 4A, the automated sample handler 70 is configured to hold a plurality of samples 70*s* in suitable sample containers 70*c* and present the samples 70*s* in their respective container 70*c* to an intake member 72 that directs the sample into the enclosed flow path 65. The sample tray 71 may hold about 50-100 samples in containers in a refrigerated or cooled enclosed compartment. Typically, the intake member 72 is configured to aspirate the sample into the flow path 65. As shown, the intake member 72 comprises a pipetter and/or needle that withdraws the desired sample amount from the container 70*c*, and then directs the sample (typically via injection through an injection port) into a conduit 73 that is in fluid communication with the flow cell 60. The pipette may rotate about 180 degrees to access tray samples or a lab automation system (TLA, workeell, etc.). However, other sample transfer means may also be used. In other embodiments, the intake member 72 can be in direct communication with the flow cell 60 without the use of an intermediate conduit 73. In particular embodiments, the samples may be directly aspirated from a source tube on the sample handler tray. The sample handler system 70 can be configured to provide rapid flow cleaning and sample delivery on about a 1-minute cycle (excluding NMR data acquisition) while reducing dilution and/or carryover.

A valved port (which may replace or be used with the injection port) may be used to help reduce unwanted sample dilution due to flow cleaning carried out between samples. In certain embodiments, the intake member 72 includes an aspiration needle that can be quickly dried using a non-contact means, such as forced air or gas, rather than conventional blotter paper to inhibit blockage of the needle. The flow cell 60 may include chromatography connectors that connect the flow cell 60 to tubing or plumbing associated with the flow path 65.

In some embodiments, the analyzer 10 can be configured to direct the aspiration to blow out the injection port immediately after injecting a first sample before pre-fetching a next sample to maintain liquid-air gaps between neighboring samples.

The sample containers 70*c* can be held in trays 71 that can be loaded and placed in queue for analysis. The samples 70*s* are electronically assigned a patient identifier to allow electronic correlation to the test results. Conventionally, the trays 71 include bar codes that are automatically read and input into the computer as electronic records as a batch of samples, thereby inhibiting adjusting test parameters for a particular sample. In some embodiments, the system 10 is configured so that the point of identification of each sample is carried out at automatically at the point of aspiration. Thus, an optic or other suitable reader can be configured to define a patient identifier to a particular sample while the sample is being aspirated. In any event, the system control software 81 can be configured to create an archivable patient data file record that includes the patient identifier (also known as an accession number) as well as a dilution factor, the NMR-derived measurement values, test date and time, and "common" rack identifier, where used, and other process information that can be electronically searched as desired for service, operational and/or audit purposes. The electronic records can be relayed to a storage location (such as a central collection site within each region or country) and/or stored locally.

In operation, NMR-derived quantitative measurement data for diagnostic clinical reports of patient biosamples can be generated by: (a) automatically serially aspirating biosamples of interest into an enclosed flow path that serially flows the biosamples into an NMR analyzer having a NMR spectroscopy instrument with a magnet and a bore at a plurality of different clinical sites; (b) automatically correlating a patient identifier to a respective patient biosample; and (c) obtaining NMR derived quantitative measurements of the target ionized constituents in the biosamples for diagnostic reports.

Referring again to FIG. 4A, the system 10 includes a controller/processor 80 that is configured with computer program code 80*s* that includes and/or is in communication with instrument automation control software 81, analytical software 82, and/or remote communication software 83. The control software 81 can primarily direct the automated operational sequences and monitoring protocols of the system 10 while the analytical software 82 typically includes software that carries out the quantitative measurements of the biosamples undergoing analysis using the NMR-spectrum thereof. For at least the analytical software 82, the processor 80 may include a digital signal processor capable of performing rapid Fourier transformations.

The remote communication software 83 can be configured to carry out and/or facilitate the communication between the local and remote sites as appropriate. The controller/processor 80 may be configured as a single processor or a plurality of processors that communicate with each other to provide the desired automated interfaces between the system components.

In certain embodiments, it may be desired to maintain the temperature of the sample undergoing NMR evaluation at a desired temperature. For example, for blood plasma and/or serum samples, it is typically desired to maintain the temperature of the sample at about 47-48° C.

In certain embodiments, the system 10 includes a plurality of spatially distributed temperature sensors along the flow path 65 that monitor the temperature of the sample undergoing analysis (not shown). The sample temperature can be determined at different times in the analysis including (a) prior to the sample entering the magnet bore 20*b*, (b) prior to initiating the RF pulse sequence, and/or (c) at the time and location of discharge from the probe, without disturbing the NMR lineshape in a manner that would impede NMR data collection/reliability. The temperature can be monitored during the NMR data acquisition (such as at least every 2-5 seconds). The sample can be actively cooled and/or heated during the evaluation to maintain a substantially constant homogeneous sample temperature without undue thermal gradients.

The system can include cooling and heating means that are configured to provide distributed heating and/or cooling for reducing hot spots in the sample. One type of heater is a capillary heater that may be slipped over the outer surface of the flow cell 60. Prototypes of a capillary heater have been custom made for LipoScience, Inc. of Raleigh, N.C., by Bruker BioSpin Corp. of Billerica, Mass. It is contemplated that a longer capillary heater can be used that extends above the flow cell 60 (where the sample is flowed into the bore 20*b* from the top) and may have a length that is sufficient to extend about a major part of the flow path length. In some embodiments, the system 10 can include a heater that is highly conductive with a relatively large thermal mass (similar to a heat sink) that is above the probe 30 (where the flow is from top to bottom), and/or above the flow cell holding portion 60*h* to thereby improve distributed heating while reducing the likelihood of overheating of the sample as it travels to the probe 30. The large thermal mass may be located outside the magnet bore 20*b*.

In some embodiments, a circulating or forced supply of temperature-controlled gas can be flowed into the magnet bore to maintain the sample at a desired temperature during the NMR analysis. The temperature of the forced air can be adjusted relatively quickly in response to in situ measured sample temperature(s). To reduce moisture that may be inadvertently directed into sensitive electronics in the probe or spectrometer, the gas can be filtered prior to introduction into the magnet bore 20*b*.

Typically, the samples are preheated from a cooled storage temperature. The auto sample handler 70 can hold the samples in a refrigerated or cooled state while in queue and gradually heat the sample in stages prior to the injection/input port to provide a sample that is preheated to a desired temperature (such as about 45-47.9° C.). Alternatively, the sample may not be heated until it is in the flow cell 60. Combinations of both heating techniques may be used. Thus, the system 10 can include thermal sensors along the path the samples travel on/in the handler 70 and/or flow path 65 that detect the temperature thereof and provide real-time feedback to allow the system 10 to automatically adjust for any deviation from predicted or norm.

In any event, the system 10 can include a sensor module that electronically communicates with processor 80 and accepts/monitors electronic data output from sensors regarding the status of the sensors.

The flow path 65 may be configured with a valved flow bypass channel (not shown) that bifurcates out of and into the flow path 65 and/or flow cell 60 to allow selected samples to be redirected back into the flow path 65 above the magnet bore 20*b* after the sample exits the probe 30 but before it reaches the waste container when a data corruption event is detected (not shown). The bypass channel could be in fluid communication with a solvent cleaner that allows automatic flushing of the bypass channel after use.

Figure 5:
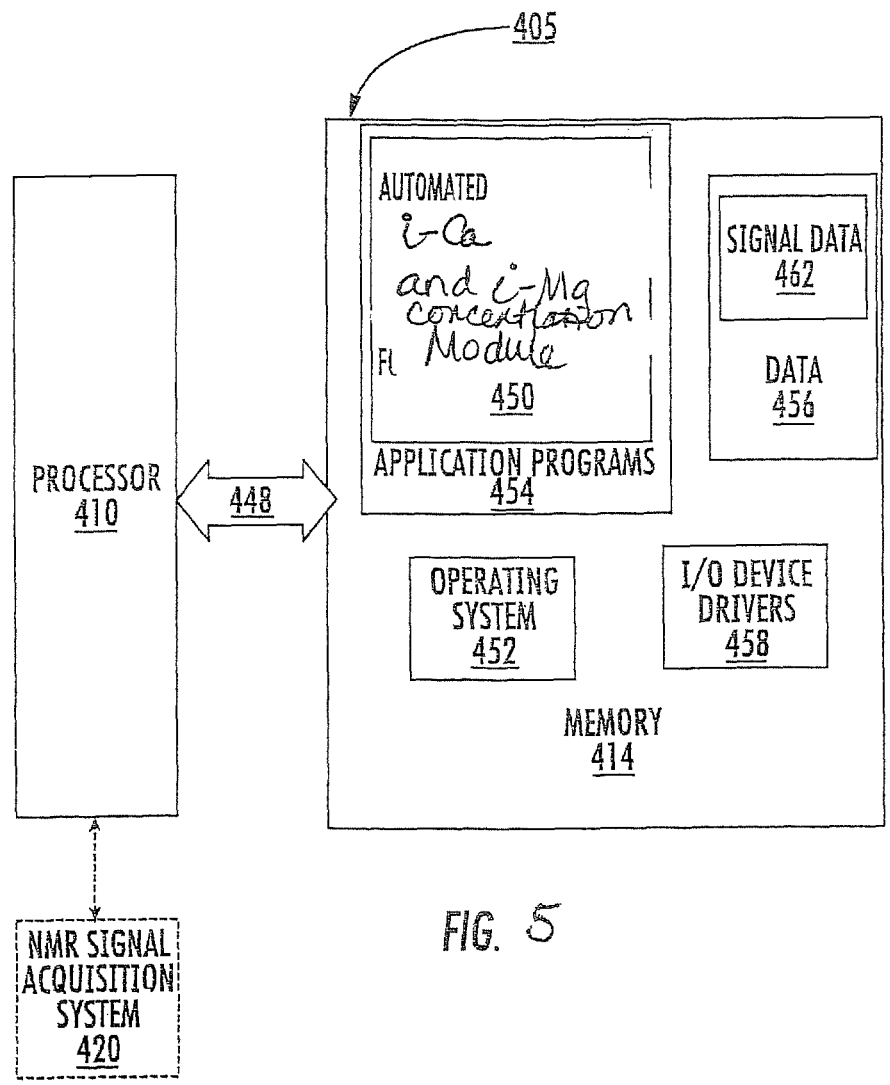
FIG. 5 is a schematic diagram of a data processing system according to embodiments of the present invention.

FIG. 5 is a block diagram of exemplary embodiments of data processing systems that illustrate systems, methods, and computer program products in accordance with embodiments of the invention. The Processor 410 communicates with the memory 414 via an address/data bus 448. The processor 410 can be any commercially available or custom microprocessor. The memory 414 is representative of the overall hierarchy of memory devices containing the software and data used to implement the functionality of the data processing system. 405. The memory 414 can include, but is not limited to, the following types of devices: cache, ROM, PROM, EPROM, EEPROM, flash memory, SRAM, and DRAM.

As shown in FIG. 5, the memory 414 may include several categories of software and data used in the data processing system 405: the operating system 452; the application programs 454; the input/output (F/O) device drivers 458; an automated i-Ca and/or i-Mg concentration calculation module 450; and data 456.

The data 456 may include NMR signal (constituent and/or composite spectrum lineshape) data 462 which may be obtained from a data or signal acquisition system 420. As will be appreciated by those of skill in the art, the operating system 452 may be any operating system suitable for use with a data processing system, such as OS/2, AIX or OS/390 from International Business Machines Corporation in Armonk, N.Y., Windows CE, Windows NT, Windows 95, Windows 98, Windows 2000, or Windows XP from Microsoft Corporation, Redmond, Wash., Palm OS from PalmSource, Inc., Sunnyvale, Calif., Mac OS from Apple Computer, Inc, UNIX, FreeBSD, or Linux, proprietary operating systems or dedicated operating systems, for example, for embedded data processing systems.

The I/O device drivers 458 typically include software routines accessed through the operation system 452 by the application programs 454 to communicate with devices such as I/O data port(s), data storage 456 and certain memory 414 components and/or the data acquisition system 420. The application programs 454 are illustrative of the programs that implement the various features of the data processing system 405 and preferably include at least one application that supports operations according to embodiments of the present invention. Finally, the data 454 represents the static and dynamic data used by the application programs 454, the operating system 452, the I/O device drivers 458, and other software programs that may reside in the memory 414.

While the present invention is illustrative, for example, with reference to the automation module 450 being an application program in FIG. 5, as will be appreciated by those of skill in the art, other configurations may also be utilized while still benefiting from the teachings of the present invention. For example, the automation module 450 may also be incorporated into the operating system 452, the I/O device drivers 458, or other such logical division of the data processing system 405. Thus the present invention should not be construed as limited to the configuration of FIG. 5, which is intended to encompass any configuration capable of carrying out the operations described herein.

Thus, embodiments of the present invention are directed to evaluating a biosample that has a suitable reagent(s) added thereto, the reagent selected for its ability to react with metabolite(s) in biological samples to produce an NMR signal that can be used for quantitation of the metabolite(s).

The invention will be described further below with the following, non-limiting examples.

EXAMPLES

Example 1

Precision, linearity, limit of detection (LOD), and limit of quantification (LOQ) studies were done using serum samples. Within-run and between-day (n=4) precision results for three levels are shown in the Table 1.

TABLE 1

| Mean, mg/dL | Within run | | Total | |
|---|---|---|---|---|
| | SD | CV % | SD | CV % |
| Ionized Ca assay N = 40 | | | | |
| 4.64 | 0.06 | 1.3 | 0.16 | 3.5 |
| 7.31 | 0.05 | 0.8 | 0.25 | 3.4 |
| 10.12 | 0.08 | 0.8 | 0.28 | 2.7 |
| Ionized Mg assay N = 40 | | | | |
| 1.06 | 0.02 | 1.9 | 0.04 | 3.4 |
| 1.75 | 0.02 | 1.1 | 0.06 | 3.7 |
| 2.48 | 0.03 | 1.1 | 0.09 | 3.8 |

With an EDTA concentration of 10 mM, the NMR assay is linear at least up to about 24 mg/dL for i-Ca and about 9.7 mg/dL for i-Mg, surpassing expected physiological ranges. The LODs are 0.22 mg/dL and 0.03 mg/dL, and the LOQs are 0.34 mg/dL and 0.09 mg/dL, for $Ca^{2+}$ and $Mg^{2+}$, respectively.

Example 2

Fresh serum specimens from volunteers were first diluted (1:1, v/v) with buffered ethylenediaminetetraaceticacid (EDTA) solution (pH=7.40, 20 mM EDTA, 100 mM $Na_2HPO_4$, and 240 mM KCl), in order to chelate ionized calcium and ionized magnesium in the free state under controlled conditions.

Quantification was achieved in a three-step process: (1) acquisition of 400 MHz proton NMR spectra of the serum specimens at 47° C. with 8 scans using established protocols on a 400 MHz NMR; (2) computer deconvolution of the proton singlet signals of the Ca and Mg complexes, appearing at 2.52 and 2.66 ppm, respectively (FIG. 2B), using proprietary software; (3) and calculation of iCa and iMg concentrations using relationships between signal areas and concentrations based on standard samples of known concentration.

The within-run and total precision results were determined by measuring aliquots of three serum samples five times per day over four different days. The mean, standard deviation (SD) and coefficient of variation (CV) were calculated.

Assay linearity was determined using chelation buffer spiked with a high concentration of iCa or iMg. The sample was then serially diluted, and the concentration was determined for each dilution in duplicate in random order in the same run. Acceptable linearity is defined by linear regression of expected versus measured concentration with error <½ *TEa (10%).

Reference range was obtained by analyzing serum samples from fifty-four apparently healthy volunteers. A questionnaire was administered to obtain relevant clinical and demographic information. Specimens remained capped and were assayed within 4 hours. This study was approved by an independent IRB and informed consent was obtained. The effect of gender on iCa and iMg was determined by t-test analysis. A p-value <0.05 was considered significant. The reference interval was calculated as the mean±2SD.

Specimen stability was assessed as follow s. Blood samples were drawn into Greiner VACUETTE serum tubes. After centrifugation, the separated serum was diluted with the buffer solution. Aliquots of the mixture were then incubated at 4° C. until measurement. The baseline measurements were assayed within 2 hours after sample preparation.

FIGS. 2A and 2B illustrate the ethylenic proton singlet signals of the Ca and Mg complexes appearing at about 2.52 ppm and about 2.66 ppm, respectively, which are used for quantification of iCa and iMg.

The results of the above evaluation are summarized below.

Stability:

The specimens are reasonably stable after preparation. Allowing for a maximum 5% change, the iCa assay is stable for up to 24 hours after chelation with EDTA, and the iMg assay is stable for 12 hours (Tables 2A, 2B). It was also evaluated that neither bilirubin nor hemolysis interfere with iCa or iMg determination (data not shown).

TABLE 2A

| NMR iCa Assay | | | | | |
|---|---|---|---|---|---|
| NMR iCa assay | | | | | |
| Specimen | Baseline | 4 Hours | 8 Hours | 12 Hours | 24 Hours |
| 1 | 1.38 | 1.40 | 1.41 | 1.44 | 1.43 |
| 2 | 1.39 | 1.38 | 1.42 | 1.41 | 1.43 |
| 3 | 1.41 | 1.43 | 1.45 | 1.43 | 1.46 |
| 4 | 1.44 | 1.48 | 1.51 | 1.49 | 1.51 |
| 5 | 1.42 | 1.44 | 1.47 | 1.46 | 1.47 |
| Mean (mM) | 1.41 | 1.43 | 1.45 | 1.45 | 1.46 |
| % difference | | 2% | 3% | 3% | 4% |

TABLE 2B

NMR iMg Assay
NMR iMg assay

| Specimen | Baseline | 4 Hours | 8 Hours | 12 Hours | 24 Hours |
|---|---|---|---|---|---|
| 1 | 0.54 | 0.56 | 0.56 | 0.54 | 0.61 |
| 2 | 0.53 | 0.55 | 0.59 | 0.59 | 0.58 |
| 3 | 0.50 | 0.51 | 0.52 | 0.55 | 0.55 |
| 4 | 0.57 | 0.61 | 0.59 | 0.57 | 0.60 |
| 5 | 0.54 | 0.53 | 0.55 | 0.54 | 0.57 |
| Mean (mM) | 0.53 | 0.55 | 0.56 | 0.56 | 0.58 |
| % difference | | 4% | 5% | 4% | 9% |

Linearity:

This assay is linear at least up to about 6.0 mM (milli Molar) for iCa and at least about 4.0 mM for iMg, surpassing physiological ranges (FIGS. 6A, 6B). The Limit of Quantitation (LOQ), which represents a (minimum) concentration that can be measured with reasonable precision (≤20%), was determined to be about 0.11 mM for iCa and about 0.13 mM for iMg. Limit of Detection (LODs) are very similar to LOQ values.

Precision:

The NMR assay showed acceptable precision compared to other clinical analyzers. The within run precision for NMR iCa assay is less than 2% while the total precision is less than 3%. The within run precision and total precision for NMR iMg assay is less than 4% (Table 3).

TABLE 3

Within-Run and Between-Day Total Precision Results
for NMR i-Ca/i-Mg Assays
Within-run and between-day total precision results for
NMR i-Ca/i-Mg assays

| Mean (mM) | Within-run | | Total | |
|---|---|---|---|---|
| | SD | CV % | SD | CV % |
| i-Ca assay (N = 40) | | | | |
| 1.46 | 0.01 | 1.0% | 0.03 | 2.1% |
| 2.16 | 0.03 | 1.3% | 0.06 | 2.6% |
| 2.94 | 0.03 | 1.0% | 0.07 | 2.3% |
| i-Mg assay (N = 40) | | | | |
| 0.58 | 0.01 | 2.5% | 0.01 | 2.5% |
| 0.80 | 0.03 | 3.2% | 0.03 | 3.2% |
| 1.05 | 0.02 | 1.8% | 0.03 | 2.9% |

The within run precision for NMR iCa assay is less than 2% and the total precision is less than 3%. The within run precision and total precision for NMR iMg assay is less than 4%.

Figure 7A:
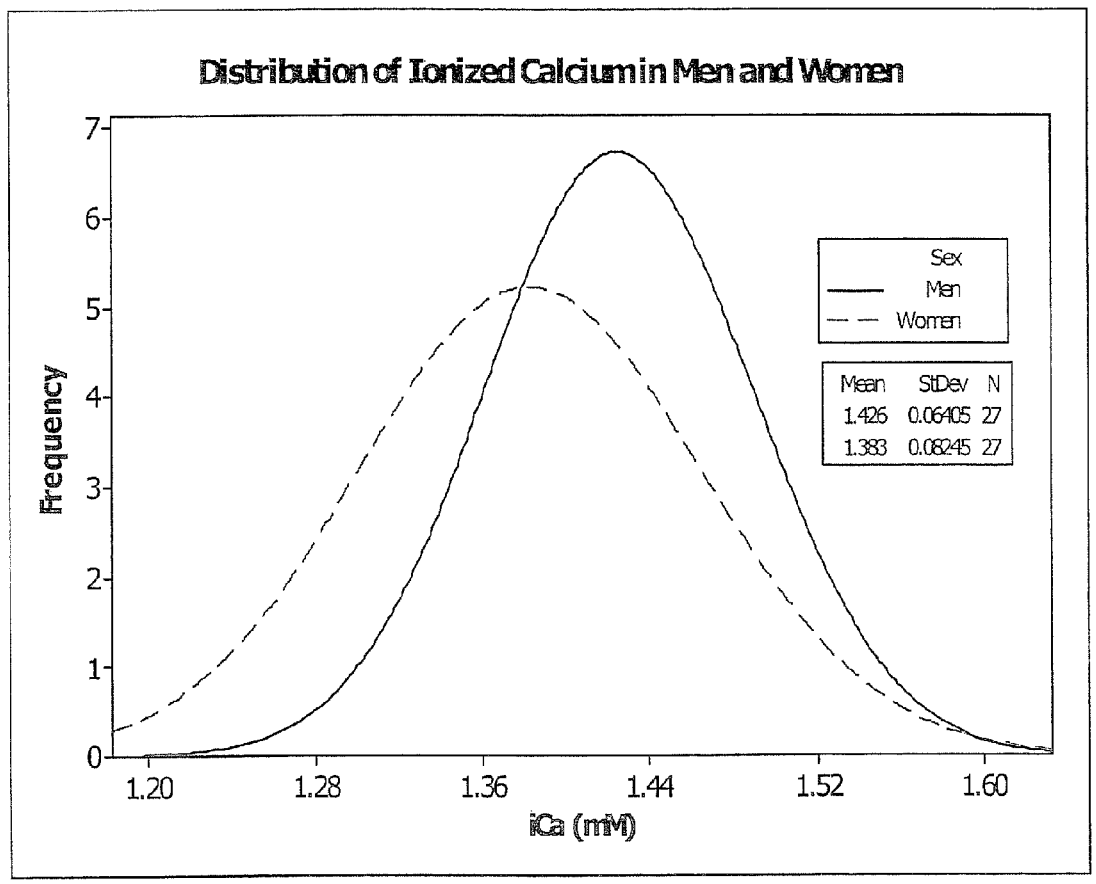
FIG. 7A is a graph of the distribution of Ionized Calcium in Men and Women (frequency versus iMg mM), with the broken line representing women.
Figure 17B:
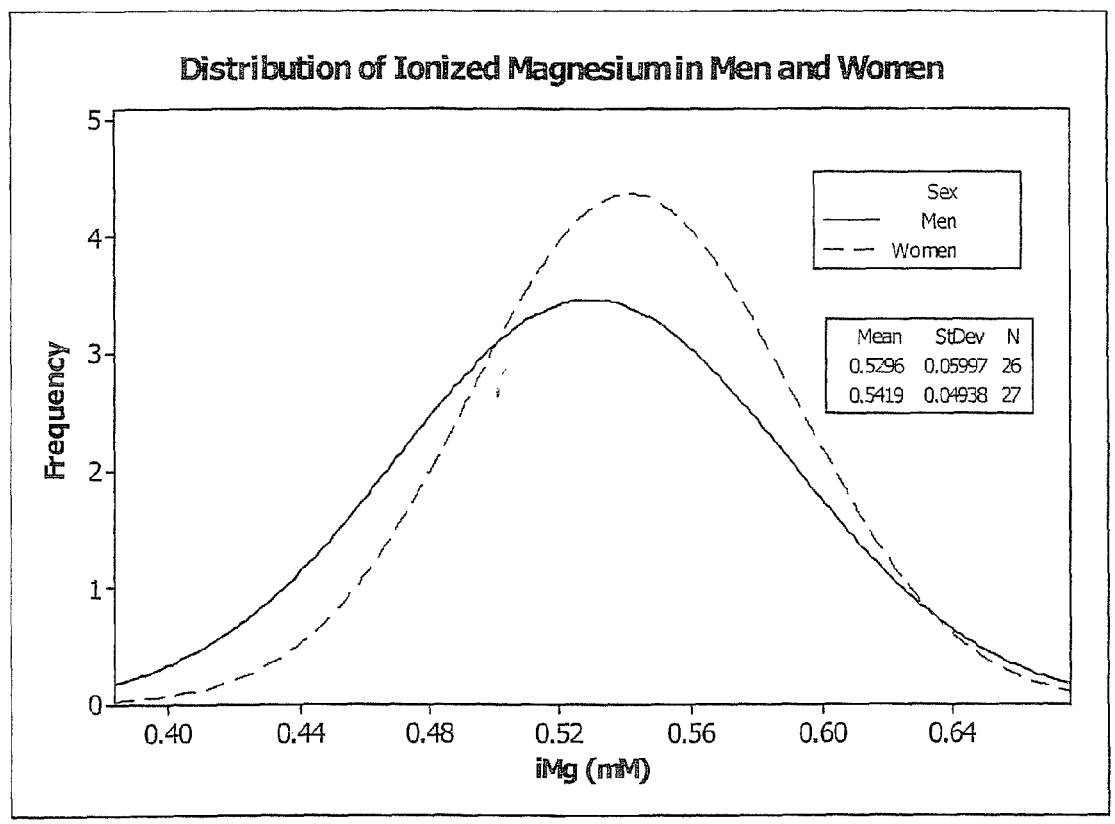

Normal Ranges:

Referring to FIG. 7B, based on 54 apparently healthy volunteer samples, a reference interval for iMg was between about 0.42-0.65 mM. There was no significant difference between men and women for iMg concentrations. Data were normally distributed around a mean of about 0.54 mM. Referring to FIG. 7A, for the iCa assay, however, there was a significant difference between men and women (1.43 mM vs 1.38 mM, respective mean, p=0.04). The reference intervals are between about 1.30-1.55 mM and between about 1.22-1.55 mM for men and women, respectively. Using data from both genders combined, the reference interval for iCa is between about 1.25-1.56 mM.

The novel NMR assay may provide a sensitive, precise and automated technical solution for measuring bioconstituents such as ionized Ca and ionized Mg directly in biosample (serum) samples. Further, unlike the conventional ISE method, ionized Mg measurement is unaffected by the presence of ionized Ca. The fully automated i-Ca/i-Mg assays can be conducted on ~150 μL serum or plasma samples that only require ~20 s of NMR time. With its reliability, small sample size, quick throughput and ease of use features, NMR iCa/iMg assay has the potential of receiving favorable clinical acceptance and improving patient care.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of measuring ionized constituents in a biosample, comprising:

transforming a biosample by adding EDTA to the biosample;

subjecting, via a nucleic magnetic resonance (NMR) spectrometer, the transformed biosample to single-pulse NMR, the obtained NMR signal data including:

first signal data corresponding to an ethylenic proton singlet region for ionized calcium; and second signal data corresponding to an ethylenic proton singlet region for ionized magnesium;

generating an NMR spectrum based on the electronically obtained NMR signal data, the NMR spectrum including:

first spectrum data for an NMR assay for ionized calcium (i-Ca) from the transformed biosample that corresponds to the ethylenic proton singlet region for ionized calcium in the first signal data; and second spectrum data for an NMR assay for ionized magnesium (i-Mg) from the transformed biosample that corresponds to the ethylenic proton singlet region for ionized magnesium in the second signal data;

deconvolving, using one or more processors, at least part of the NMR spectrum, the at least part of the NMR spectrum including:

the first spectrum data corresponding to the ethylenic proton singlet region for ionized calcium; and the second data corresponding to the ethylenic proton singlet region for ionized magnesium, wherein the deconvolving resolves at least one of the ionized calcium or ionized magnesium ethylenic proton singlet regions from background due to lipoproteins in the biosample;

identifying, using the one or more processors, a single peak for each of one or both of the ionized calcium and the ionized magnesium based on the deconvolution;

calculating, using the one or more processors, at least one of:
    a quantitative concentration of ionized calcium in the biosample based the identified single peak for the ionized calcium; and
    a quantitative concentration of ionized magnesium in the biosample based the identified single peak for the ionized magnesium; and
generating an electronic report that includes the at least one of the quantitative concentration of ionized calcium or the quantitative concentration of the ionized magnesium, wherein the NMR spectrometer is a 400 MHz spectrometer;
    first signal data corresponding to the ethylenic proton singlet region for ionized calcium is centered at 2.52 ppm and the second signal data corresponding to the ethylenic proton singlet region for ionized magnesium is centered at 2.66 ppm;
    the calculating the at least one of the quantitative concentration of ionized calcium and the quantitative concentration of ionized magnesium includes:
    using a relationship for determining the quantitative concentration of ionized calcium that is linear up to about 6.0 mM and has a within run and total precision with a coefficient of variation (% cv) that is less than 3%; or
    using a relationship for determining the quantitative concentration of ionized magnesium that is linear up to about 4.0 mM and has a within run and total precision with a coefficient of variation (% cv) that is less than 4%.

2. The method according to claim 1, wherein the biosample is transformed by adding the EDTA to the biosample while the biosample is at a temperature of between about 20-25 degrees Celsius to chelate the ionized calcium and ionized magnesium in a free state, then heating the chelated sample to a temperature of between 45-47.9 degrees Celsius for the obtaining step.

3. The method according to claim 1, further comprising electronically comparing data from the deconvolved NMR signal data with a priori calibration data corresponding to standard samples with known concentrations of ionized calcium and magnesium to determine the concentrations of i-Ca and i-Mg in the biosample.

4. The method according to claim 1, wherein the biosample is a blood, serum or plasma sample.

5. The method according to claim 1, wherein the biosample is cerebral spinal fluid or urine.

6. The method according to claim 1, further comprising automatically flowing biosamples to a flow probe in a magnet bore associated with the NMR spectrometer, wherein the method further comprises electronically correlating a patient accession number or identifier with a respective biosample before or during the electronically obtaining of the NMR signal data.

7. The method according to claim 1, wherein the biosample for the obtaining step is between about 25 µL to 150 µL.

8. The method according to claim 1, wherein the electronic report includes a plurality of defined gender-specific acceptable ranges or measurement levels, and wherein the plurality of defined gender-specific acceptable ranges or measurement levels include a reference interval between about 1.30-1.55 mM for men and a reference interval between about 1.22-1.55 mM for women.

9. The method of claim 1, wherein the single pulse NMR is performed in a manner such that the transformed biosample is held at a temperature between 45 and 47.9 degrees Celsius in a flow probe of the NMR spectrometer and the NMR spectrometer electronically obtains the NMR signal data with an NMR signal acquisition time of less than 1 minute.

10. A method of measuring constituents in a biosample, comprising:
    chelating a biosample by adding EDTA to the biosample;
    electronically obtaining single pulse NMR signal data from a proton NMR spectrum of the chelated biosample and deconvolving the proton NMR spectrum, wherein the NMR signal data is based on data collected while the biosample is held at a temperature of between 45-47.9 degrees Celsius in a NMR spectrometer;
    programmatically determining a quantitative concentration of ionized calcium (i-Ca) and ionized magnesium (i-Mg) in the chelated biosample based on the obtained and deconvolved NMR data, wherein the concentration of i-Ca is calculated using NMR data of an ethylenic proton singlet signal that is centered at 2.52 ppm, wherein the concentration of i-Mg is calculated using NMR data of an ethylenic proton singlet region that is centered at 2.66 ppm, wherein the determining is carried out using a defined analysis for ionized calcium that is linear up to about 6.0 mM with a within run and total precision with a coefficient of variation (% cv) that is less than 3%, and wherein the determining is carried out so that a defined analysis for ionized magnesium is linear up to about 4.0 mM with a within run and total precision with a coefficient of variation (% cv) that is less than 4%; and
    providing the determined concentrations in a patient test report that provides the ionized calcium (i-Ca) concentration and the ionized magnesium (i-Mg) concentration with (i) a reference interval for i-Ca that is between about 1.30-1.55 mM for men and between about 1.22-1.55 for women and (ii) a reference interval for i-Mg that is between about 0.42-0.65 mM for both genders.

11. A method of calculating quantitative concentrations of ionized calcium and ionized magnesium in biosamples, the method comprising:
    subjecting, via an NMR spectrometer, a biosample to single-pulse NMR to generate an NMR spectrum that includes: first signal data, for an NMR assay for ionized calcium from the biosample that corresponds to the ethylenic proton singlet region for ionized calcium in the NMR data, and second signal data, for an NMR assay for ionized magnesium from the biosample that corresponds to the ethylenic proton singlet region for ionized magnesium in the NMR signal data;
    deconvolving, using one or more processors: the first signal data corresponding to the ethylenic proton singlet region for ionized calcium to resolve the ethylenic proton singlet region for ionized calcium from signal due to lipoproteins in the biosample; and the second signal data corresponding to the ethylenic proton singlet region for ionized magnesium to resolve the ethylenic proton singlet region for ionized magnesium from signal due to lipoproteins in the biosample;
    identifying, using the one or more processors, an ionized-calcium single peak for the ionized calcium in the deconvoluted at least part of the NMR signal, the ionized-calcium single peak being centered at 2.52 ppm;
    identifying, using the one or more processors, an ionized-magnesium single peak for the ionized magnesium in the deconvoluted at least part of the NMR signal, the ionized-magnesium single peak being centered at 2.66 ppm;

calculating, using the one or more processors, at least one of: a quantitative concentration of ionized calcium in the biosample based on a characteristic of the ionized-calcium single peak based for the ionized calcium in the deconvoluted at least part of the NMR signal, wherein and the ionized calcium NMR assay is linear up to about 6.0 mM, and has a within run and total precision with a coefficient of variation (% cv) that is less than 3%; and a quantitative concentration of ionized magnesium in the biosample based on a characteristic of the ionized magnesium single peak based for the ionized magnesium in the deconvoluted at least part of the NMR signal, wherein the ionized magnesium NMR assay that is linear up to about 4.0 mM, and has a within run and total precision with a coefficient of variation (% cv) that is less than 4%; and generating an electronic report that includes: the quantitative concentration of ionized calcium and the quantitative concentration of ionized magnesium.

12. A computer program product for determining concentrations of ionized constituents in respective patient plasma and/or serum samples, the computer program product comprising a non-transitory computer readable storage medium having computer readable program code embodied in said medium, said computer-readable program code comprising computer readable program code configured to perform actions including:

receiving a single-pulse proton NMR composite spectrum generated, at least in part, by an NMR spectrometer in response to NMR processing of a biosample, and the proton NMR composite spectrum includes a defined ethylenic singlet peak region for ionized calcium that is centered at 2.52 ppm of the proton NMR spectrum, and the proton NMR composite spectrum includes a defined ethylenic singlet peak region for ionized magnesium that is centered at 2.66 ppm of the proton NMR spectrum;

deconvolving the obtained proton NMR composite spectrum to generate a first area of a first curve associated with the defined ethylenic singlet peak region for ionized calcium resolved from background peaks due to lipoproteins, and a second area of a second curve associated with the defined ethylenic singlet peak region for ionized magnesium resolved from background peaks due to lipoproteins;

determining a first concentration measurement of ionized calcium based on the first area of the first curve and a relationship for determining the quantitative concentration of ionized calcium that is linear up to about 6.0 mM and has a within run and total precision with a coefficient of variation (% cv) that is less than 3%;

determining a second concentration measurement of ionized magnesium based on the second area of the second curve and a relationship for determining the quantitative concentration of ionized magnesium that is linear up to about 4.0 mM and has a within run and total precision with a coefficient of variation (% cv) that is less than 4%; and generating an electronic report that includes the first concentration measurement of ionized calcium and the second concentration measurement of ionized magnesium.

13. A method of measuring ionized constituents in biosamples, comprising:

subjecting, via a proton NMR spectrometer, a biosample to single-pulse NMR in a manner such that the biosample is held at a temperature between 45 and 47.9 Celsius in the NMR spectrometer; and the NMR spectrometer electronically generates a proton NMR spectrum based on collecting data corresponding to the temperature-held transformed biosample with an NMR signal acquisition time of less than 1 minute, the proton NMR spectrum including:
first signal data corresponding to an ethylenic proton singlet region for ionized calcium; and
second signal data corresponding to an ethylenic proton singlet region for ionized magnesium;

programmatically deconvolving, using one or more processors, the proton NMR spectrum of the biosample wherein the deconvolving resolves at least one of the ionized calcium or ionized magnesium ethylenic proton singlet regions from background due to lipoproteins in the biosample;

determining, using the one or more processors, a concentration of ionized calcium based on:
the deconvolution; and
an ionized calcium NMR assay that interrogates a defined ethylenic peak-centered at 2.52 ppm of the proton NMR spectrum that is linear up to about 6.0 mM and that has a within run and total precision with a coefficient of variation (% cv) that is less than 3%;

determining, using the one or more processors, a concentration of ionized magnesium based on:
the deconvolution; and
an ionized magnesium NMR assay that interrogates a defined ethylenic proton singlet peak region for magnesium centered at 2.66 ppm of the proton NMR spectrum that is linear up to about 4.0 mM and that has a within run and total precision with a coefficient of variation (% cv) that is less than 4%;

calculating, using the one or more processors, measurements of lipoprotein subclass data using the proton NMR spectrum; and generating an electronic report that identifies the lipoprotein subclass data, the concentration of ionized calcium, the concentration of ionized magnesium, a reference interval for ionized calcium that is between about 1.30-1.55 mM for men and between about 1.22-1.55 for women, and a reference interval for ionized magnesium that is between about 0.42-0.65 mM for both genders.

14. The method according to claim 13, wherein the electronic report includes a plurality of defined gender-specific acceptable ranges or measurement levels, and wherein the plurality of defined gender-specific acceptable ranges or measurement levels include a male mean of the measured i-Ca of about 1.43 mM and a female mean of the measured i-Ca of about 1.38 mM.

* * * * *